(12) United States Patent
Skiba et al.

(10) Patent No.: US 8,329,099 B1
(45) Date of Patent: *Dec. 11, 2012

(54) REIGNITING FLAME IN VOLATILE ORGANIC COMPOUND DEVICE

(75) Inventors: Leo Skiba, Nassau Bay, TX (US); Rex Moses, Nassau Bay, TX (US); Keith Adams, Galveston, TX (US); Jack Clark, Houston, TX (US); Bradley O'Keefe, Houston, TX (US); Kevin Moses, League City, TX (US); Andrew Reiter, Houston, TX (US)

(73) Assignee: LDARtools, Inc., League City, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,493

(22) Filed: Sep. 26, 2011

Related U.S. Application Data

(63) Continuation of application No. 11/668,367, filed on Jan. 29, 2007, now Pat. No. 8,034,290.

(51) Int. Cl.
*G01N 27/00* (2006.01)
*G01N 7/00* (2006.01)
*G01N 21/00* (2006.01)
*G01N 31/00* (2006.01)
*G01N 33/00* (2006.01)
*G01N 31/12* (2006.01)

(52) U.S. Cl. ............... 422/54; 422/83; 422/94

(58) Field of Classification Search ............ 422/54, 422/94

See application file for complete search history.

(56) References Cited

U.S. PATENT DOCUMENTS

| 3,853,455 A | * | 12/1974 | Riordan et al. ............... 431/80 |
| 3,985,509 A | * | 10/1976 | Trone et al. .................. 422/54 |
| 4,346,055 A | | 8/1982 | Murphy et al. |
| H000572 H | | 2/1989 | Hansen |
| 5,206,818 A | | 4/1993 | Speranza |
| 5,356,594 A | | 10/1994 | Neel et al. |
| 6,341,287 B1 | | 1/2002 | Sziklai et al. |
| 6,438,535 B1 | | 8/2002 | Benjamin et al. |
| 6,478,849 B1 | | 11/2002 | Taylor et al. |
| 6,545,278 B1 | | 4/2003 | Mottier et al. |
| 6,609,090 B1 | | 8/2003 | Hickman et al. |

(Continued)

FOREIGN PATENT DOCUMENTS

WO  2006-022648 A1  3/2006

OTHER PUBLICATIONS

Response to Office Action (Feb. 21, 2012) and USPTO Office Action (Nov. 18, 2011); U.S. Appl. No. 12/359,196 (Moses, et al.).

(Continued)

*Primary Examiner* — Jill Warden
*Assistant Examiner* — Charles D Hammond
(74) *Attorney, Agent, or Firm* — Pramudji Law Group PLLC; Ari Pramudji

(57) ABSTRACT

Reigniting a flame in a volatile organic compound (VOC) detector in the event that the flame has gone out. In one implementation, a signal is received at a handheld personal computer indicating that a flame in the VOC detector has gone out. The flame in the VOC detector may then be reignited using the handheld personal computer and a Bluetooth enabled device facilitating communication between the handheld personal computer and the VOC detector.

29 Claims, 3 Drawing Sheets

U.S. PATENT DOCUMENTS

| | | | |
|---|---|---|---|
| 6,672,129 | B1 | 1/2004 | Frederickson et al. |
| 6,680,778 | B2 | 1/2004 | Hinnrichs et al. |
| 6,722,185 | B2 | 4/2004 | Lawson et al. |
| 7,017,386 | B2 | 3/2006 | Liu et al. |
| 7,103,610 | B2 | 9/2006 | Johnson et al. |
| 7,136,904 | B2 | 11/2006 | Bartek et al. |
| 7,369,945 | B2 | 5/2008 | Miller et al. |
| 7,588,726 | B1 * | 9/2009 | Mouradian et al. ............. 422/83 |
| 7,657,384 | B1 | 2/2010 | Moses |
| 7,840,366 | B1 | 11/2010 | Moses et al. |
| 7,908,118 | B2 | 3/2011 | Trowbridge et al. |
| 8,034,290 | B1 * | 10/2011 | Skiba et al. ..................... 422/54 |
| 2002/0026339 | A1 | 2/2002 | Frankland et al. |
| 2002/0080032 | A1 | 6/2002 | Smith et al. |
| 2002/0094498 | A1 | 7/2002 | Rodriguez-Rodriguez et al. |
| 2003/0012696 | A1 | 1/2003 | Millancourt |
| 2003/0081214 | A1 | 5/2003 | Mestha et al. |
| 2003/0085714 | A1 | 5/2003 | Keyes et al. |
| 2004/0226345 | A1 | 11/2004 | McCoy et al. |
| 2004/0258213 | A1 | 12/2004 | Beamon et al. |
| 2005/0000981 | A1 | 1/2005 | Peng et al. |
| 2005/0053104 | A1 | 3/2005 | Kulp et al. |
| 2005/0117641 | A1 | 6/2005 | Xu et al. |
| 2005/0262995 | A1 | 12/2005 | Kilkis |
| 2006/0020186 | A1 | 1/2006 | Brister et al. |
| 2006/0220888 | A1 | 10/2006 | Germouni et al. |
| 2006/0235611 | A1 | 10/2006 | Deaton et al. |
| 2006/0286945 | A1 | 12/2006 | Reznik et al. |
| 2007/0000310 | A1 | 1/2007 | Yamartino et al. |
| 2008/0021717 | A1 | 1/2008 | Kaartinen et al. |
| 2008/0063298 | A1 | 3/2008 | Zhou et al. |
| 2008/0092625 | A1 | 4/2008 | Hinnrichs |
| 2008/0120043 | A1 | 5/2008 | Miller et al. |
| 2008/0231719 | A1 | 9/2008 | Benson et al. |
| 2009/0315669 | A1 | 12/2009 | Lang et al. |
| 2010/0211333 | A1 | 8/2010 | Pruet et al. |

OTHER PUBLICATIONS

USPTO Office Action (Nov. 22, 2011); U.S. Appl. No. 12/463,770 (Moses).

RCE Amendment (Jun. 22, 2011), Advisory Action (Jun. 7, 2011), Response After Final (May 23, 2011), Final Office Action (Mar. 22, 2011), Response to Office Action (Dec. 27, 2010), and Office Action (Sep. 27, 2010); U.S. Appl. No. 12/133,920 (Moses, et al).

USPTO Office Action (Nov. 18, 2011); U.S. Appl. No. 12/359,196 (Moses, et al.).

USPTO Final Action (Nov. 28, 2011), Response to Office Action (Aug. 29, 2011), and Office Action (May 27, 2011); U.S. Appl. No. 12/474,504 (Bolinger, et al.).

Sylvers, Eric; Wireless: The story of 'Wi'—Technology—International Herald Tribune; Apr. 2006; http://www.nytimes.com/2006/04/17/technology/17iht-wireless18.1550306.html?pagewanted=print (retrieved May 17, 2011).

"Bluetooth Tutorial—Specifications"; Palo Wireless: Bluetooth Resource Center [online]; Jan. 5, 2006; retrieved Dec. 23, 2009 via Internet Archive Wayback Machine.

*Environmental Analytics, Inc. v. TMX2, Inc. and LDAR Solutions, Ltd.*; Case 4:08-cv-03353; USDC, Southern District of Texas; First Amended Complaint; Dec. 10, 2008.

"2nd Annual Fugitive Emissions—Leak Detection and Repair Symposium"; ISA Technical Conference Brochure; Nov. 2002.

"Introducing the Allegro CX(TM) Field Computer"; Product Newswire (product announcement); Jun. 21, 2004.

"New from Accutech, Wireless Acoustic Monitor Field Units Make Fugitive Emissions Monitoring Compliance Easy"; Product Announcement/Description; Feb. 10, 2004.

"LDARManager™ Makes Fugitive Emission Monitoring A Breeze TISCOR launches its newest product for Leak Detection and Repair"; product announcement/description; Nov. 8, 2008.

* cited by examiner

REIGNITING FLAME IN VOLATILE ORGANIC COMPOUND DEVICE

CROSS-REFERENCE TO RELATED APPLICATIONS

This application is a continuation of U.S. patent application Ser. No. 11/668,367, filed Jan. 29, 2007, and to be issued as U.S. Pat. No. 8,034,290 on Oct. 11, 2011, which is incorporated herein by reference.

BACKGROUND

1. Field of the Invention

Implementations of various technologies described herein are directed to volatile organic compound (VOC) detection and to various methods and/or systems for igniting a flame in a volatile organic compound (VOC) detector, e.g., reigniting a flame that has been extinguished in a volatile organic compound (VOC) detector.

2. Description of the Related Art

The following descriptions and examples do not constitute an admission as prior art by virtue of their inclusion within this section.

Industrial plants that handle volatile organic compounds (VOCs) sometimes experience unwanted emissions of those compounds into the atmosphere from point sources, such as smokestacks, and non-point sources, such as valves, pumps, and/or vessels containing the VOCs. Emissions from non-point sources typically occur due to leakage of the VOCs from joints and/or seals and may be referred to herein as "fugitive emissions". Fugitive emissions from control valves typically occur as leakage through the packing set around the valve stem. Control valves used in demanding service conditions involving large temperature fluctuations and frequent movements of the valve stem commonly suffer accelerated deterioration of the valve stem packing set.

The United States Environmental Protection Agency (EPA) has promulgated regulations specifying maximum permitted leakage of certain hazardous air pollutants, such as benzene, toluene, 1,1,1-trichloroethane, from certain hardware or fixtures, e.g., control valves. The regulations require facility operators to perform periodic surveys of the emissions from all control valves and pump seals. The survey interval frequency may be monthly, quarterly, semiannual, or annual. If the facility operator can document that a certain percentage of valves and pumps with excessive leakage are below a prescribed minimum, the required surveys become less frequent. Thus, achieving a low percentage of leaking valves reduces the number of surveys required per year, which may result in large cost savings.

Fugitive emissions are typically monitored using a VOC detector, which may also be referred to as a vapor analyzer. Due to the location of the control valves and a tendency to jar the VOC detector during operation, the flame inside the VOC detector may often go out during detection. When this happens, the technician operating the VOC detector may need to reignite the flame, e.g., by manually reigniting the flame. Manual reignition has a number of disadvantages, including having to unstrap the VOC detector from the back of the technician. If the flame extinguishes while the technician is in the process of climbing up a ladder on a structure, e.g., en route to a location where detection will take place, then the entire detection process is disrupted and often, for safety reasons, the technician not only has to stop climbing the ladder, but changes direction and goes back down the ladder, so that the VOC detector can be safely unstrapped and the flame manually reignited. Accordingly, there is an ongoing need for the methods and systems disclosed below.

SUMMARY

Described herein are implementations of various technologies of a method for igniting a flame in a volatile organic compound (VOC) detector. In one implementation, the method includes transmitting a first signal to the VOC detector through a wireless device. The signal is configured to ignite a flame in the VOC detector.

In another implementation, the method may include receiving a signal at a handheld personal computer indicating that a flame in the VOC detector is extinguished and reigniting the flame in the VOC detector using a wireless device configured to facilitate communication between the handheld personal computer and the VOC detector.

Also described herein are implementations of various technologies for a volatile chemical (VOC) detection system, which may include a VOC detector and a handheld personal computer in communication with the VOC detector. The handheld personal computer may be configured to control an operation of the VOC detector. The VOC detection system may further include a wireless device in communication with the VOC detector and the handheld personal computer. The wireless device may be configured to facilitate communication between the VOC detector and the handheld personal computer.

Still further, described herein are implementations of various technologies for a volatile chemical (VOC) detector, which may include a processor and a memory comprising program instructions executable by the processor to receive a first signal indicating that a flame in the VOC detector is extinguished; send a first command to a signal inverter to ground port B of the VOC detector for a first predetermined amount of time and apply a first positive voltage to port B once the first predetermined amount of time has lapsed; receive a second signal indicating an option to reignite the flame in the VOC detector; and send a second command to the signal inverter to ground port C of the VOC detector for a second predetermined amount of time and apply a second positive voltage to port C once the second predetermined amount of time has lapsed.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

The following paragraphs generally describe implementations of various techniques directed to various methods and systems for igniting a flame in a volatile organic compound (VOC) detector or reigniting a flame that has been extinguished. In one implementation, the VOC detection system includes a VOC detector in communication with a handheld personal computer (PC), a signal inverter coupled to the VOC detector and a Bluetooth enabled device for facilitating communication between the VOC detector and the handheld PC. The Bluetooth enabled device communicates with the handheld PC wirelessly.

In operation, when a flame inside the VOC detector extinguishes, the VOC detector sends an error message to the handheld PC via the Bluetooth enabled device. In response, the technician may send a first command through the handheld PC to the signal inverter. Upon receipt of the first command, the signal inverter grounds port B of the VOC detector for a predetermined amount of time and applies a positive voltage after the predetermined amount of time has lapsed. Upon detection that its port B was grounded for the predetermined amount of time and the positive voltage is applied to the port, the VOC detector clears the error message and sends an option to reignite the flame to the handheld PC via the Bluetooth enabled device. Upon receipt of this option, the technician may then send a second command through the handheld PC to the signal inverter. Upon receipt of the second command, the signal inverter grounds port C of the VOC detector for a predetermined amount of time and applies a positive voltage after the predetermined amount of time has lapsed. Upon detecting that port C has been grounded for the predetermined amount of time and the positive voltage is applied to port C, the VOC detector reignites the flame. One or more techniques for reigniting a flame in the VOC detector in accordance with various implementations are described in more detail with reference to FIGS. 1-3 in the following paragraphs.

Figure 1:
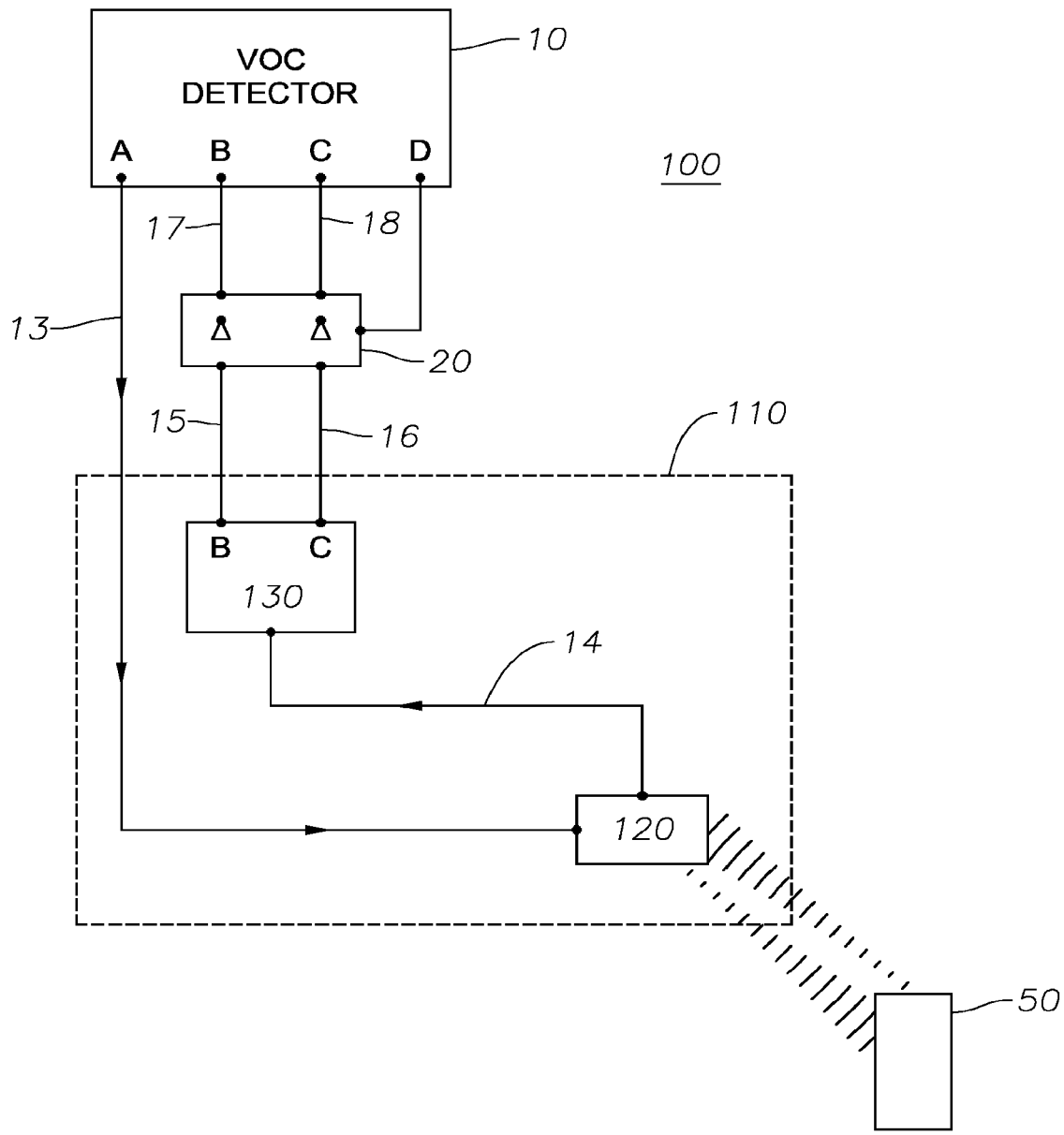
FIG. 1 illustrates a schematic diagram of a VOC detection system in accordance with one or more implementations of various technologies described herein

FIG. 1 illustrates a VOC detection system 100 in accordance with one or more implementations of various technologies described herein. The VOC detection system 100 may also be referred to as a toxic vapor analyzer (TVA). The VOC detection system 100 may include a VOC detector or analyzer 10 configured to detect volatile organic chemicals, emissions gases, nitroaromatics, chemical warfare agents and the like. In one implementation, the VOC detector 10 is TVA-1000 available from The Foxboro Company out of Massachusetts, USA. However, it should be understood that some implementations may use other types of VOC detectors. The VOC detector 10 may include an organic or inorganic vapor monitor using a flame ionization detector (FID) or both an FID and a photoionization detector (PID). The VOC detector 10 may be coupled to a signal inverter 20, which may be configured to invert a positive voltage signal to ground. Although the signal inverter 20 is described herein as being configured to invert a positive signal to ground, it should be understood that in some implementations depending on the configuration of the VOC detector 10, the signal inverter 20 may be configured to invert a positive voltage to a negative voltage or invert a negative voltage signal to a positive voltage signal. Likewise, although the VOC detector 10 is described as operating with a signal inverter 20, it should be understood that in some implementations the VOC detector 10 may operate with other devices having the same or similar functionalities as the signal inverter 20, such as an electro-mechanical relay, a solid state relay, or an integrated circuit that would operate to pull a positive voltage signal to ground.

The signal inverter 20 may be coupled to the VOC detector 10 via cable 17 at port B and via cable 18 at port C. Various cables described herein may be made of copper. However, it should be understood that the various cables may be made from other types of material, such as fiber optic, aluminum and the like. Port D of the VOC detector 10 may be connected to ground.

The VOC detector 10 may further be coupled to a Bluetooth enabled device 110. As such, port A of the VOC detector 10 may be coupled to a transceiver 120 portion of the Bluetooth enabled device 110 via cable 13. The Bluetooth enabled device 110 is described in more detail in the paragraphs below.

The signal inverter 20 may also be coupled to the Bluetooth enabled device 110 via cable 15 and cable 16. In one implementation, the signal inverter 20 may be a Quadruple Line Receiver™ available from Texas Instruments headquartered in Dallas, Tex. However, it should be understood that other implementations may use a signal inverter that may have a different configuration or design and manufactured by companies other than Texas Instruments.

The term "Bluetooth enabled device" as used herein means any device that is enabled with Bluetooth technology. Bluetooth is a wireless technology that operates in the unlicensed Industrial, Scientific, and Medical (ISM) radio band of 2.4 GHz. Bluetooth technology includes a number of protocols that allow Bluetooth enabled devices to operate in a peer-to-peer environment forming piconets. The Bluetooth protocol and specification may be found in: *Bluetooth system; Specification* Volumes 1 and 2, Core and Profiles: Version 1.1, 22 Feb. 2001. The Bluetooth enabled device 110 may be configured to facilitate communication between the VOC detector 10, the signal inverter 20 and a handheld personal computer (PC) 50, which will be described in more detail in the paragraphs below. The Bluetooth enabled device 110 may include a transceiver 120 and a processor 130. The processor 130 may be coupled to the transceiver 120 by cable 14.

The processor 130 may include a central processing unit (CPU), a system memory and a system bus that couples various system components including the system memory to the CPU. The system memory may include a read only memory (ROM) and a random access memory (RAM). A basic input/output system (BIOS), containing the basic routines that help transfer information between elements within the processor 130, such as during start-up, may be stored in the ROM.

The Bluetooth enabled device 110 may be in communication with the handheld PC 50 wirelessly. Although implementations of various technologies are described herein with reference to the Bluetooth enabled device 110, it should be understood that some implementations may use other type of wireless data communication or protocol, such as Spread Spectrum, Broadband, Wi-Fi and the like.

Figure 2:
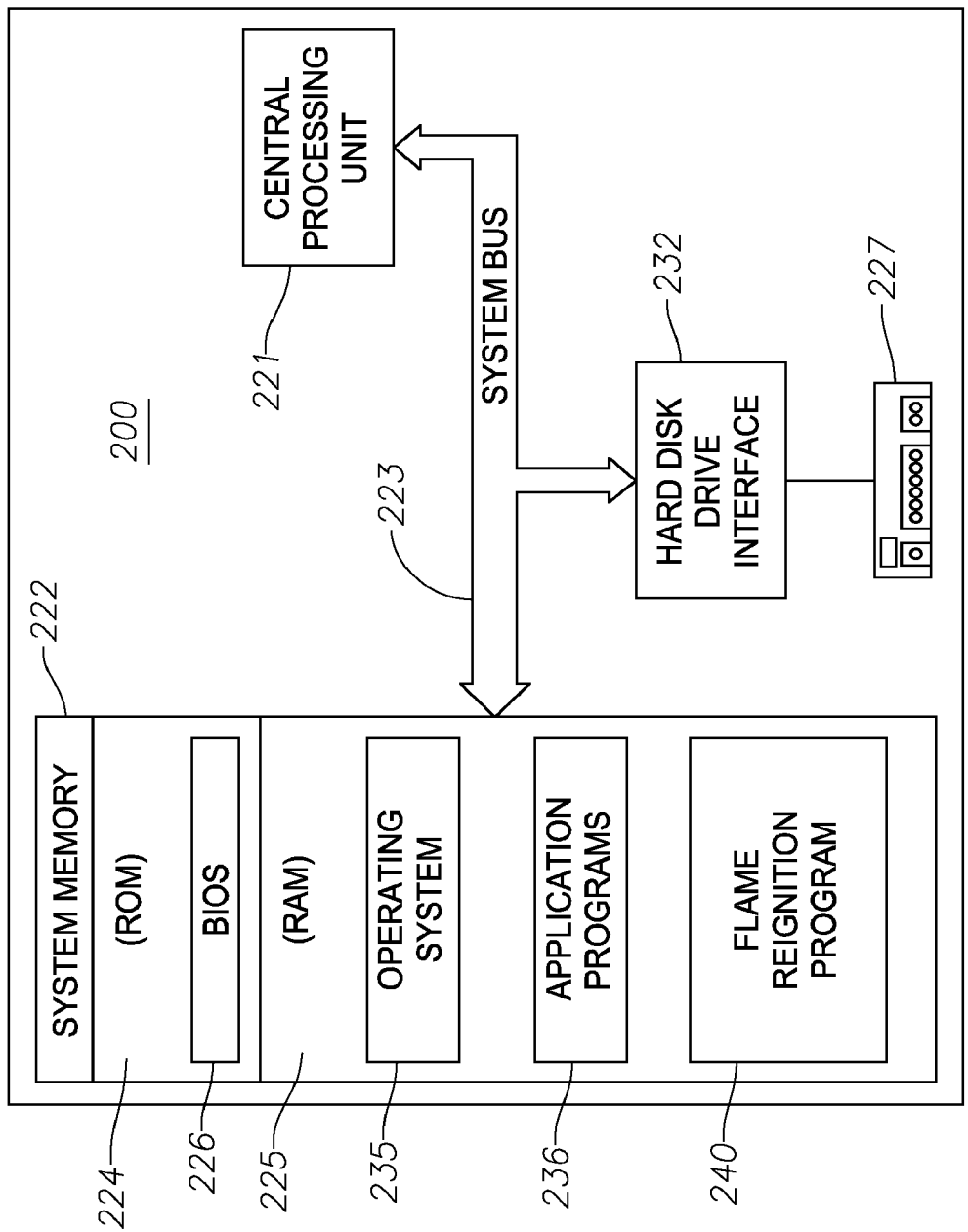
FIG. 2 illustrates a schematic diagram of a handheld personal computer in accordance with one or more implementations of various technologies described herein.

FIG. 2 illustrates a schematic diagram of a handheld PC 200 in accordance with one or more implementations of various technologies described herein. The handheld PC 200 may include a central processing unit (CPU) 221, a system memory 222 and a system bus 223 that couples various system components including the system memory 222 to the CPU 221. Although only one CPU is illustrated in FIG. 2, it should be understood that in some implementations the handheld PC 200 may include more than one CPU. The system bus 223 may be any of several types of bus structures, including a memory bus or memory controller, a peripheral bus, and a local bus using any of a variety of bus architectures. By way of example, and not limitation, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 222 may include a read only memory (ROM) 224 and a random access memory (RAM) 225. A basic input/output system (BIOS) 226, containing the basic routines that help transfer information between elements within the handheld PC 200, such as during start-up, may be stored in the ROM 224.

The handheld PC 200 may further include a hard disk drive 227 for reading from and writing to a hard disk. The hard disk drive 227 may be connected to the system bus 223 by a hard disk drive interface 232. The drives and their associated computer-readable media may provide nonvolatile storage of computer-readable instructions, data structures, program modules and other data for the handheld PC 200.

The handheld PC 200 may further include computer-readable media that may be accessed by the CPU 221. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the CPU 221. Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on ROM 224 or RAM 225, including an operating system 235, one or more application programs 236 and a flame reignition program 240. The operating system 235 may be any suitable operating system that may control the operation of a networked personal or server computer, such as Windows® XP, Mac OS® X, Unix-variants (e.g., Linux® and BSD®), and the like. The flame reignition program 240 will be described in more detail with reference to FIG. 3 in the paragraphs below.

It should be understood that the various technologies described herein may be implemented in connection with hardware, software or a combination of both. Thus, various technologies, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the various technologies. In the case of program code execution on programmable computers, the computing device may include a processor, a storage medium readable by the processor (including volatile and non-volatile memory and/or storage elements), at least one input device, and at least one output device. One or more programs that may implement or utilize the various technologies described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

Figure 3:
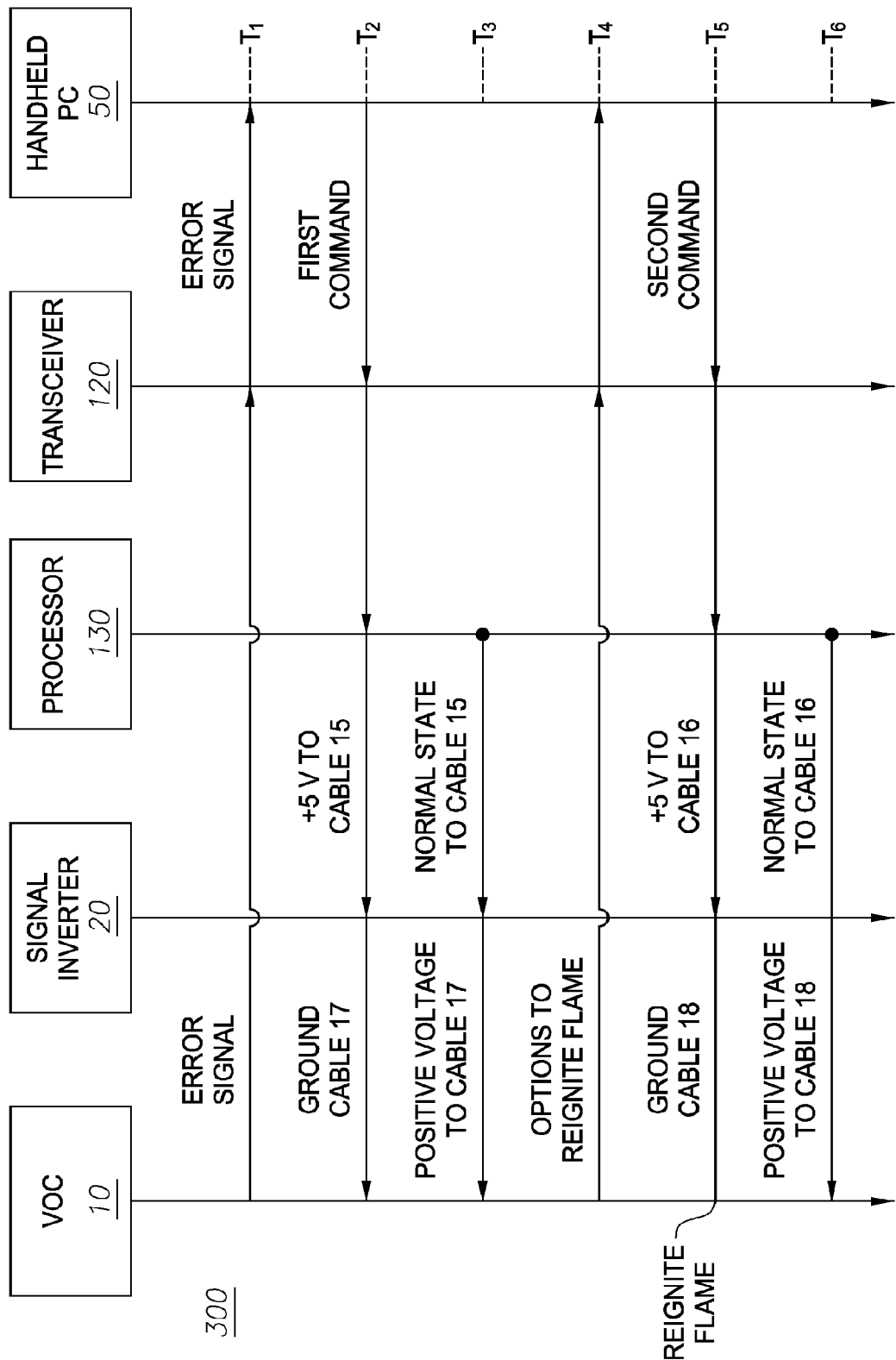
FIG. 3 illustrates a signal diagram for reigniting a flame in the VOC detector in accordance with one or more implementations of various technologies described herein.

FIG. 3 illustrates a signal diagram 300 for reigniting a flame in the VOC detector 10 in accordance with one or more implementations of various technologies described herein. At time T1, when the flame extinguishes in the VOC detector 10, the VOC detector 10 may send an error signal through port A via cable 13 to the transceiver 120, which may then forward the error signal to the handheld PC 50 wirelessly.

In response to receiving the error signal, the handheld PC 50 may display the error message to the user/operator. For example, the handheld PC 50 may display WARNING: FLAME OUT. In one implementation, the same message may be displayed on the screen of the VOC detector 10.

At time T2, upon seeing the display, the user may send a first command from the handheld PC 50 to the processor 130 through the transceiver 120 wirelessly. The first command may include a first portion and a second portion. In one implementation, the first portion and the second portion may be separated by a predetermined time delay, e.g., about 1 second to about 3 seconds. Upon receipt of the first portion, the processor 130 may send a positive 5 volts signal along cable 15 to the signal inverter 20, which may then apply a zero voltage signal to cable 17, thereby grounding port B of the VOC 10. A positive voltage is typically applied to port B during operation. In one implementation, the signal inverter 20 may ground cable 17 using port D, which is connected to ground.

At time T3, after the predetermined time delay has lapsed, upon receipt of the second portion, the processor 130 may apply a normal state signal along cable 15 to the signal inverter 20, which may then remove the zero voltage previously applied to cable 17 and apply a positive voltage typically applied to port B during operation.

In this manner, the first command may operate as a toggling signal. The first portion may be configured to ground cable 17, while the second portion may be configured to stop the grounding cable 17 and apply an operating voltage to cable 17. In one implementation, the first portion may be ST, 0808 and the second portion may be ST, 0800.

At time T4, upon detecting that port B, to which cable 17 is connected, has been switched to ground for a predetermined amount of time (e.g., about 1 second to about 3 seconds) and returned to its operating voltage, the VOC detector 10 may clear the error message on its screen and display a set of options for addressing the flame out situation on its screen.

One option for addressing the flame out situation is to reignite the flame. As such, the VOC detector 10 may send the set of options to the transceiver 120 through cable 13. The transceiver 120 may then forward the set of options to the handheld PC 50 wirelessly. Alternatively, the VOC detector 10 may send only the option to reignite the flame to the transceiver 120.

At time T5, upon receipt of an option to reignite the flame, the user may wirelessly send a second command from the handheld PC 50 to the processor 130 through the transceiver 120. The second command may include a first portion and a second portion. The first portion and the second portion may be separated by a predetermined time delay, e.g., about 1 second to 3 seconds. Upon receipt of the first portion of the second command, the processor 130 may apply a positive 5 volts signal along cable 16 to the signal inverter 20, which may then switch cable 18 to ground. As mentioned above, the signal inverter 20 may use port D, which is connected to ground, to ground cable 18.

At time T6, after the predetermined time delay has lapsed, upon receipt of the second portion of the second command, the processor 130 may apply a normal state signal along cable 16 to the signal inverter 20, which may then remove the zero voltage previously applied to cable 18 and apply a positive voltage typically applied to cable 18 during operation.

In this manner, the second command may operate as a toggling signal. The first portion may be configured to ground cable 18, while the second portion may be configured to stop the grounding cable 18 and apply an operating voltage to cable 18. In one implementation, the first portion may be ST, 0404 and the second portion may be ST, 0400.

Upon detecting that port C, to which cable 18 is connected, has been switched to ground for the predetermined amount of time (e.g., about 1 second to about 3 seconds) and returned to its operating voltage, the VOC detector 10 may reignite the flame.

Although the commands that control the operation of the VOC detector 10, e.g., for reigniting the flame, have been described with reference to the handheld PC 50, it should be understood that in some implementations the commands may be sent from the Bluetooth enabled device 110. For instance, the commands to clear the error message displayed due to the flame having been extinguished may be sent via a switch on the Bluetooth enabled device 110. The commands to reignite the flame may be sent using the same switch or in combination with another switch on the Bluetooth enabled device 110.

Although implementations of various technologies described herein are described with reference to a handheld PC, it should be understood that some implementations may be operational with other types of computing systems, such as laptop devices, multiprocessor systems, microprocessor-based systems, programmable consumer electronics, network PCs, minicomputers, personal computers and the like.

The various technologies described herein may be implemented in the general context of computer-executable instructions, such as program modules, being executed by a computer. Generally, program modules include routines, programs, objects, components, data structures, etc. that perform particular tasks or implement particular abstract data types. The various technologies described herein may also be implemented in distributed computing environments where tasks are performed by remote processing devices that are linked through a communications network, e.g., by hardwired links, wireless links, or combinations thereof. In a distributed computing environment, program modules may be located in both local and remote computer storage media including memory storage devices.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for igniting a flame in a volatile organic compound (VOC) detector, comprising:
    sending a first command to a signal inverter coupled to the VOC detector, wherein the first command is configured to clear an error message in the VOC detector by (i) grounding a first port of the VOC detector and (ii) removing the ground from the first port after a predetermined amount of time has lapsed; and
    sending a second command to the signal inverter, wherein the second command is configured to ignite a flame in the VOC detector by (i) grounding a second port of the VOC detector and (ii) removing the ground from the second port, thereby igniting the flame.

2. The method of claim 1, wherein the first command and second command are sent to the signal inverter using a wireless device.

3. The method of claim 2, wherein the first command and second command are sent by activating a switch on the wireless device.

4. The method of claim 1, wherein the first command comprises a first portion configured to cause the signal inverter to ground the first port of the VOC detector for the predetermined amount of time.

5. The method of claim 4, wherein the predetermined amount of time ranges from about one second to about three seconds.

6. The method of claim 1, wherein the second command comprises a first portion configured to cause the signal inverter to ground the second port of the VOC detector for a predetermined amount of time.

7. The method of claim 6, wherein the second command further comprises a second portion configured to cause the signal inverter to remove the ground from the second port after the predetermined amount of time has lapsed.

8. The method of claim 4, further comprising receiving an option to reignite the flame in the VOC detector after the first port has been grounded for the predetermined amount of time.

9. The method of claim 8, wherein the second command is sent to the VOC detector in response to receiving the option to reignite the flame in the VOC detector.

10. The method of claim 1, wherein the first command and the second command are sent to the signal inverter from a handheld personal computer through a wireless device facilitating communication between the handheld personal computer and the signal inverter.

11. The method of claim 1, wherein the first command comprises applying a positive voltage to the first port of the VOC detector after removing the ground.

12. The method of claim 1, wherein the second command comprises applying a positive voltage to the second port of the VOC detector after removing the ground.

13. A volatile organic compound (VOC) detection system, comprising:
    a VOC detector; and
    a wireless device in communication with the VOC detector, wherein the wireless device is configured to control an operation of the VOC detector and comprises a processor and memory having program instructions executable by the processor to:

send a first command to the VOC detector, wherein the first command is configured to clear an error message in the VOC detector by (i) grounding a first port of the VOC detector and (ii) removing the ground from the first port after a predetermined amount of time has lapsed; and send a second command to the VOC detector, wherein the second command is configured to ignite a flame in the VOC detector by (i) grounding a second port of the VOC detector and (ii) removing the ground from the second port, thereby igniting the flame.

14. The VOC detection system of claim 13, wherein the first command is transmitted by activating a switch on the wireless device.

15. The VOC detection system of claim 13, wherein the second command is transmitted by activating a switch on the wireless device.

16. The VOC detection system of claim 13, wherein the VOC detector is configured to send an error signal to the wireless device upon detecting that the flame in the VOC detector has gone out.

17. The VOC detection system of claim 13, further comprising a signal inverter coupled between the wireless device and the VOC detector, and wherein the first command causes the signal inverter to ground the first port of the VOC detector for the predetermined amount of time and remove the ground from the first port after the predetermined amount of time has lapsed.

18. The VOC detection system of claim 13, further comprising a signal inverter coupled between the wireless device and the VOC detector, and wherein the second command causes the signal inverter to ground the second port of the VOC detector for a second predetermined amount of time and remove the ground from the second port after the second predetermined amount of time has lapsed.

19. A handheld personal computer for operating a volatile chemical (VOC) detector, comprising:
a processor; and
a memory comprising program instructions executable by the processor to:
send a first command to the VOC detector, wherein the first command is configured to clear an error message by (i) grounding a first port of the VOC detector and (ii) removing the ground from the first port after a predetermined amount of time has lapsed; and
send a second command to the VOC detector to reignite a flame.

20. The handheld personal computer of claim 19, wherein the second command is configured to cause a signal inverter coupled to the VOC detector to ground a second port of the VOC detector for a predetermined amount of time and stop the grounding of the second port after the predetermined amount of time has lapsed.

21. A handheld personal computer for operating a volatile chemical (VOC) detector, comprising:
a processor; and
a memory comprising program instructions executable by the processor to:

receive a first signal from the VOC detector having an error message indicating that a flame in the VOC detector is extinguished;

send a first command to the VOC detector to clear the error message, wherein the first command is configured to cause a signal inverter coupled to the VOC detector to ground a first port of the VOC detector for a predetermined amount of time and stop the grounding of the first port after the predetermined amount of time has lapsed;

receive a second signal from the VOC detector indicating an option to reignite the flame in the VOC detector; and send a second command to the VOC detector to reignite the flame.

22. The handheld personal computer of claim 21, wherein the signal inverter is an electro-mechanical relay, a solid state relay or an integrated circuit.

23. A non-transitory computer-readable medium having stored thereon computer-executable instructions which, when executed by a computer, cause the computer to:
send a first command to a signal inverter coupled to a volatile organic compound (VOC) detector, wherein the first command is configured to clear an error message in the VOC detector by (i) grounding a first port of the VOC detector and (ii) removing the ground from the first port after a predetermined amount of time has lapsed; and
send a second command to the signal inverter, wherein the second command is configured to ignite a flame in the VOC detector by (i) grounding a second port of the VOC detector and (ii) removing the ground from the second port, thereby igniting the flame.

24. The computer-readable medium of claim 23, wherein the first command comprises a first portion configured to cause the signal inverter to ground the first port of the VOC detector for the predetermined amount of time.

25. The computer-readable medium of claim 24, wherein the first command further comprises a second portion configured to cause the signal inverter to remove the ground from the first port after the predetermined amount of time has lapsed.

26. The computer-readable medium of claim 23, wherein the second command comprises a first portion configured to cause the signal inverter to ground the second port of the VOC detector for a predetermined amount of time.

27. The computer-readable medium of claim 26, wherein the second command further comprises a second portion configured to cause the signal inverter to remove the ground from the second port after the predetermined amount of time has lapsed.

28. The computer-readable medium of claim 24, further comprising receiving an option to reignite the flame in the VOC detector after the first port has been grounded for the predetermined amount of time.

29. The computer-readable medium of claim 28, wherein the second command is sent to the VOC detector in response to receiving the option to reignite the flame in the VOC detector.

* * * * *